United States Patent
Brannan

(10) Patent No.: US 10,076,383 B2
(45) Date of Patent: Sep. 18, 2018

(54) ELECTROSURGICAL DEVICE HAVING A MULTIPLEXER

(75) Inventor: Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 867 days.

(21) Appl. No.: 13/358,129

(22) Filed: Jan. 25, 2012

(65) Prior Publication Data

US 2013/0190751 A1    Jul. 25, 2013

(51) Int. Cl.
*A61B 18/12* (2006.01)
*A61B 18/18* (2006.01)
(Continued)

(52) U.S. Cl.
CPC ............ *A61B 18/1815* (2013.01); *A61B 2017/00106* (2013.01); *A61B 2018/00333* (2013.01); *A61B 2018/00351* (2013.01); *A61B 2018/00511* (2013.01); *A61B 2018/00541* (2013.01); *A61B 2018/00547* (2013.01); *A61B 2018/00559* (2013.01); *A61B 2018/00577* (2013.01);
(Continued)

(58) Field of Classification Search
CPC ........ A61N 1/025; A61N 1/3702; A61N 1/08; A61N 1/3937; G06F 19/3418; G06F 19/3406; Y10T 29/49002; Y10T 29/49117; Y10T 156/10; Y10T 156/1089; Y10T 29/49204; Y10T 29/53204; G06Q 50/22; A61B 5/00; A61B 5/0015; A61B 2018/00839; A61B 2018/00642; A61B 2018/00648; A61B 2018/00755; A61B 2018/00892; A61B 5/01; A61B 5/02; A61B 5/02055; A61B 5/0245; A61B 5/03; A61B 5/7264; Y10S 128/92

USPC ...... 606/32–34, 41–42; 607/1–2, 34–35, 115
See application file for complete search history.

(56) References Cited

U.S. PATENT DOCUMENTS

| 4,291,708 A | 9/1981 | Frei et al. |
| 4,416,276 A | 11/1983 | Newton et al. |

(Continued)

FOREIGN PATENT DOCUMENTS

| CN | 1103807 | 6/1995 |
| CN | 1617689A A | 5/2005 |

(Continued)

OTHER PUBLICATIONS

U.S. Appl. No. 08/136,098, filed Oct. 14, 1993, Roger A. Stern.
(Continued)

*Primary Examiner* — Deborah Malamud

(57) ABSTRACT

An electrosurgical system includes an electrosurgical generator configured to provide electrosurgical energy to an electrosurgical device coupled thereto which, in turn, delivers electrosurgical energy to tissue. The electrosurgical device may include a plurality of sensors configured to detect one or more tissue properties and output a detected tissue property signal relating thereto. One or more multiplexers having a plurality of channels are electrically connected to each of the corresponding plurality of sensors. The multiplexer(s) may be configured to receive the detected tissue property signal from each sensor of the plurality of sensors and output at least one output signal along a signal line. The signal line is configured to connect to the electrosurgical generator to control a power output of the electrosurgical generator. A channel select algorithm is configured to automatically select channels from the plurality of channels.

16 Claims, 6 Drawing Sheets

(51) Int. Cl.
*A61B 17/00* (2006.01)
*A61B 18/00* (2006.01)
*A61B 90/00* (2016.01)

(52) U.S. Cl.
CPC .............. *A61B 2018/00702* (2013.01); *A61B 2018/00791* (2013.01); *A61B 2018/00875* (2013.01); *A61B 2018/00892* (2013.01); *A61B 2018/1838* (2013.01); *A61B 2018/1853* (2013.01); *A61B 2018/1861* (2013.01); *A61B 2090/065* (2016.02)

(56) References Cited

U.S. PATENT DOCUMENTS

| | | | |
|---|---|---|---|
| 4,416,277 A | 11/1983 | Newton et al. | |
| 4,448,547 A | 5/1984 | Wickersheim | |
| 4,514,619 A | 4/1985 | Kugelman | |
| 4,549,533 A | 10/1985 | Cain et al. | |
| 4,560,286 A | 12/1985 | Wickersheim | |
| 4,569,345 A | 2/1986 | Manes | |
| 4,617,939 A | 10/1986 | Brown et al. | |
| 4,658,820 A | 4/1987 | Klicek | |
| 4,669,475 A | 6/1987 | Turner | |
| 4,739,759 A | 4/1988 | Rexroth et al. | |
| 4,741,348 A | 5/1988 | Kikuchi et al. | |
| 4,744,372 A | 5/1988 | Kikuchi et al. | |
| 4,747,416 A | 5/1988 | Kikuchi et al. | |
| 4,753,248 A | 6/1988 | Engler et al. | |
| 4,827,911 A | 5/1989 | Broadwin et al. | |
| 4,852,579 A | 8/1989 | Gilstad et al. | |
| 4,860,752 A | 8/1989 | Turner | |
| 4,860,770 A | 8/1989 | Kikuchi et al. | |
| 4,873,995 A | 10/1989 | Kikuchi et al. | |
| 4,955,377 A | 9/1990 | Lennox et al. | |
| 4,955,383 A | 9/1990 | Faupel | |
| 4,974,587 A | 12/1990 | Turner et al. | |
| 5,006,119 A | 4/1991 | Acker et al. | |
| 5,024,668 A | 6/1991 | Peters et al. | |
| 5,025,810 A | 6/1991 | Kikuchi et al. | |
| 5,033,478 A | 7/1991 | Kikuchi et al. | |
| 5,148,814 A | 9/1992 | Kikuchi et al. | |
| 5,157,603 A | 10/1992 | Scheller et al. | |
| 5,282,840 A | 2/1994 | Hudrlik | |
| 5,313,943 A | 5/1994 | Houser et al. | |
| 5,318,563 A | 6/1994 | Malis et al. | |
| 5,320,101 A | 6/1994 | Faupel et al. | |
| 5,341,807 A | 8/1994 | Nardella | |
| 5,370,645 A | 12/1994 | Klicek et al. | |
| 5,370,672 A | 12/1994 | Fowler et al. | |
| 5,423,808 A | 6/1995 | Edwards et al. | |
| 5,443,463 A | 8/1995 | Stern et al. | |
| 5,496,312 A | 3/1996 | Klicek | |
| 5,507,743 A | 4/1996 | Edwards et al. | |
| 5,531,774 A | 7/1996 | Schulman et al. | |
| 5,534,018 A | 7/1996 | Wahlstrand et al. | |
| 5,536,267 A | 7/1996 | Edwards et al. | |
| 5,558,672 A | 9/1996 | Edwards et al. | |
| 5,569,241 A | 10/1996 | Edwards | |
| 5,599,345 A | 2/1997 | Edwards et al. | |
| 5,599,346 A | 2/1997 | Edwards et al. | |
| 5,658,322 A | 8/1997 | Fleming | |
| 5,672,173 A | 9/1997 | Gough et al. | |
| 5,672,174 A | 9/1997 | Gough et al. | |
| 5,683,384 A | 11/1997 | Gough et al. | |
| 5,696,441 A | 12/1997 | Mak et al. | |
| 5,712,543 A | 1/1998 | Sjostrom | |
| 5,722,975 A | 3/1998 | Edwards et al. | |
| 5,735,847 A | 4/1998 | Gough et al. | |
| 5,743,903 A | 4/1998 | Stern et al. | |
| 5,769,847 A | 6/1998 | Panescu et al. | |
| 5,800,484 A | 9/1998 | Gough et al. | |
| 5,810,804 A | 9/1998 | Gough et al. | |
| 5,843,021 A | 12/1998 | Edwards et al. | |
| 5,863,290 A | 1/1999 | Gough et al. | |
| 5,897,552 A | 4/1999 | Edwards et al. | |
| 5,904,709 A | 5/1999 | Arndt et al. | |
| 5,919,219 A | 7/1999 | Knowlton | |
| 5,928,229 A | 7/1999 | Gough et al. | |
| 5,944,022 A | 8/1999 | Nardella et al. | |
| 5,951,547 A | 9/1999 | Gough et al. | |
| 5,964,755 A | 10/1999 | Edwards | |
| 6,017,354 A | 1/2000 | Culp et al. | |
| 6,022,346 A | 2/2000 | Panescu et al. | |
| 6,024,740 A | 2/2000 | Lesh et al. | |
| 6,024,743 A | 2/2000 | Edwards | |
| 6,044,283 A | 3/2000 | Fein et al. | |
| 6,052,607 A | 4/2000 | Edwards et al. | |
| 6,056,744 A | 5/2000 | Edwards | |
| 6,059,780 A | 5/2000 | Gough et al. | |
| 6,071,280 A | 6/2000 | Edwards et al. | |
| 6,071,281 A | 6/2000 | Burnside et al. | |
| 6,073,051 A | 6/2000 | Sharkey et al. | |
| 6,080,150 A | 6/2000 | Gough | |
| 6,083,223 A | 7/2000 | Baker | |
| 6,086,544 A | 7/2000 | Hibner et al. | |
| 6,090,123 A | 7/2000 | Culp et al. | |
| 6,096,031 A | 8/2000 | Mitchell et al. | |
| 6,117,101 A | 9/2000 | Diederich et al. | |
| 6,123,702 A | 9/2000 | Swanson et al. | |
| 6,134,476 A | 10/2000 | Arndt et al. | |
| 6,152,923 A | 11/2000 | Ryan | |
| 6,162,184 A | 12/2000 | Swanson et al. | |
| 6,171,304 B1 | 1/2001 | Netherly et al. | |
| 6,175,768 B1 | 1/2001 | Arndt et al. | |
| 6,183,468 B1 | 2/2001 | Swanson et al. | |
| 6,216,704 B1 | 4/2001 | Ingle et al. | |
| 6,231,569 B1 | 5/2001 | Bek et al. | |
| 6,238,388 B1 | 5/2001 | Ellman et al. | |
| 6,241,753 B1 | 6/2001 | Knowlton | |
| 6,243,654 B1 | 6/2001 | Johnson et al. | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,267,760 B1 | 7/2001 | Swanson | |
| 6,273,862 B1 | 8/2001 | Privitera et al. | |
| 6,280,441 B1 | 8/2001 | Ryan | |
| 6,290,715 B1 | 9/2001 | Sharkey et al. | |
| 6,293,941 B1 | 9/2001 | Strul et al. | |
| 6,293,943 B1 | 9/2001 | Panescu et al. | |
| 6,322,584 B2 | 11/2001 | Ingle et al. | |
| 6,329,778 B1 | 12/2001 | Culp et al. | |
| 6,330,479 B1 | 12/2001 | Stauffer | |
| 6,350,263 B1 | 2/2002 | Wetzig et al. | |
| 6,350,276 B1 | 2/2002 | Knowlton | |
| 6,366,818 B1 | 4/2002 | Bolmsjo | |
| 6,370,408 B1 | 4/2002 | Merchant et al. | |
| 6,386,032 B1 | 5/2002 | Lemkin et al. | |
| 6,413,255 B1 | 7/2002 | Stern | |
| 6,416,491 B1 | 7/2002 | Edwards et al. | |
| 6,424,186 B1 | 7/2002 | Quimby et al. | |
| 6,425,912 B1 | 7/2002 | Knowlton | |
| 6,427,089 B1 | 7/2002 | Knowlton | |
| 6,430,446 B1 | 8/2002 | Knowlton | |
| 6,458,121 B1 | 10/2002 | Rosenstock et al. | |
| 6,494,880 B1 | 12/2002 | Swanson et al. | |
| 6,494,882 B1 | 12/2002 | Lebouitz et al. | |
| 6,500,172 B1 | 12/2002 | Panescu et al. | |
| 6,511,478 B1 | 1/2003 | Burnside et al. | |
| 6,544,260 B1 | 4/2003 | Markel et al. | |
| 6,546,270 B1 | 4/2003 | Goldin et al. | |
| 6,551,311 B2 | 4/2003 | Lee et al. | |
| 6,569,159 B1 | 5/2003 | Edwards et al. | |
| 6,585,664 B2 | 7/2003 | Burdorff et al. | |
| 6,599,288 B2 | 7/2003 | Maguire et al. | |
| 6,605,085 B1 | 8/2003 | Edwards | |
| 6,613,047 B2 | 9/2003 | Edwards | |
| 6,622,731 B2 | 9/2003 | Daniel et al. | |
| 6,624,702 B1 | 9/2003 | Dening | |
| 6,652,513 B2 | 11/2003 | Panescu et al. | |
| 6,652,514 B2 | 11/2003 | Ellman et al. | |
| 6,652,515 B1 | 11/2003 | Maguire et al. | |
| 6,656,177 B2 | 12/2003 | Truckai et al. | |
| 6,662,053 B2 | 12/2003 | Borkan | |
| 6,663,624 B2 | 12/2003 | Edwards et al. | |

(56) References Cited

U.S. PATENT DOCUMENTS

| | | |
|---|---|---|
| 6,672,151 B1 | 1/2004 | Schultz et al. |
| 6,673,070 B2 | 1/2004 | Edwards et al. |
| 6,693,782 B1 | 2/2004 | Lash |
| 6,749,624 B2 | 6/2004 | Knowlton |
| 6,752,767 B2 | 6/2004 | Turovskiy et al. |
| 6,784,405 B2 | 8/2004 | Flugstad et al. |
| 6,786,905 B2 | 9/2004 | Swanson et al. |
| 6,802,843 B2 | 10/2004 | Truckai et al. |
| 6,845,264 B1 | 1/2005 | Skladnev et al. |
| 6,860,881 B2 | 3/2005 | Sturm et al. |
| 6,867,744 B2 | 3/2005 | Toncich et al. |
| 6,942,660 B2 | 9/2005 | Pantera et al. |
| 6,962,587 B2 | 11/2005 | Johnson et al. |
| 6,994,707 B2 | 2/2006 | Ellman et al. |
| 6,997,925 B2 | 2/2006 | Maguire et al. |
| 7,025,765 B2 | 4/2006 | Balbierz et al. |
| 7,053,752 B2 | 5/2006 | Wang et al. |
| 7,089,063 B2 | 8/2006 | Lesh et al. |
| 7,094,231 B1 | 8/2006 | Ellman et al. |
| 7,097,640 B2 | 8/2006 | Wang et al. |
| 7,108,696 B2 | 9/2006 | Daniel et al. |
| 7,128,739 B2 | 10/2006 | Prakash et al. |
| 7,160,293 B2 | 1/2007 | Sturm et al. |
| 7,160,296 B2 | 1/2007 | Pearson et al. |
| 7,194,294 B2 | 3/2007 | Panescu et al. |
| 7,197,363 B2 | 3/2007 | Prakash et al. |
| 7,258,690 B2 | 8/2007 | Sutton et al. |
| 7,267,683 B2 | 9/2007 | Sharkey et al. |
| 7,278,991 B2 | 10/2007 | Morris et al. |
| 7,282,061 B2 | 10/2007 | Sharkey et al. |
| 7,311,702 B2 | 12/2007 | Tallarida et al. |
| 7,344,533 B2 | 3/2008 | Pearson et al. |
| 7,344,534 B2 | 3/2008 | Long |
| 7,364,546 B2 | 4/2008 | Panescu et al. |
| 7,400,930 B2 | 7/2008 | Sharkey et al. |
| 7,422,582 B2 | 9/2008 | Malackowski et al. |
| 7,422,586 B2 | 9/2008 | Morris et al. |
| 7,439,736 B2 | 10/2008 | Meaney et al. |
| 7,468,042 B2 | 12/2008 | Turovskiy et al. |
| 7,479,140 B2 | 1/2009 | Ellman et al. |
| 7,517,351 B2 | 4/2009 | Culp et al. |
| 7,582,084 B2 | 9/2009 | Swanson et al. |
| 7,585,296 B2 | 9/2009 | Edwards et al. |
| 7,601,149 B2 | 10/2009 | DiCarlo et al. |
| 7,625,371 B2 | 12/2009 | Morris et al. |
| 7,675,429 B2 | 3/2010 | Cernasov |
| 7,736,357 B2 | 6/2010 | Lee, Jr. et al. |
| 7,736,358 B2 | 6/2010 | Shores et al. |
| 7,799,020 B2 | 9/2010 | Shores et al. |
| 7,840,253 B2 | 11/2010 | Tremblay et al. |
| 7,846,108 B2 | 12/2010 | Turovskiy et al. |
| 7,862,559 B2 | 1/2011 | Prakash et al. |
| 7,879,029 B2 | 2/2011 | Jimenez |
| 7,941,202 B2 | 5/2011 | Hetke et al. |
| 8,057,465 B2 | 11/2011 | Sliwa, Jr. et al. |
| 8,147,486 B2 | 4/2012 | Honour et al. |
| 8,211,096 B2 | 7/2012 | Pless et al. |
| 8,257,349 B2 | 9/2012 | Orszulak |
| 2001/0047183 A1 | 11/2001 | Privitera et al. |
| 2002/0120261 A1 | 8/2002 | Morris et al. |
| 2002/0156472 A1 | 10/2002 | Lee et al. |
| 2003/0199863 A1 | 10/2003 | Swanson et al. |
| 2004/0030367 A1 | 2/2004 | Yamaki et al. |
| 2004/0097805 A1 | 5/2004 | Verard et al. |
| 2005/0240239 A1 | 10/2005 | Boveja et al. |
| 2005/0283148 A1 | 12/2005 | Janssen et al. |
| 2006/0085054 A1 | 4/2006 | Zikorus et al. |
| 2006/0106375 A1 | 5/2006 | Werneth et al. |
| 2006/0191926 A1 | 8/2006 | Ray et al. |
| 2006/0289528 A1 | 12/2006 | Chiu et al. |
| 2007/0060989 A1 | 3/2007 | Deem et al. |
| 2007/0078454 A1 | 4/2007 | McPherson |
| 2007/0100405 A1 | 5/2007 | Thompson et al. |
| 2007/0198006 A1 | 8/2007 | Prakash et al. |
| 2007/0260237 A1 | 11/2007 | Sutton et al. |
| 2007/0293855 A1 | 12/2007 | Sliwa, Jr. et al. |
| 2007/0299435 A1 | 12/2007 | Crowe et al. |
| 2008/0004536 A1 | 1/2008 | Baxi et al. |
| 2008/0082095 A1 | 4/2008 | Shores et al. |
| 2008/0125775 A1 | 5/2008 | Morris |
| 2008/0154259 A1 | 6/2008 | Gough et al. |
| 2008/0183251 A1 | 7/2008 | Azar et al. |
| 2008/0234574 A1 | 9/2008 | Hancock et al. |
| 2008/0262489 A1 | 10/2008 | Steinke |
| 2008/0281310 A1 | 11/2008 | Dunning et al. |
| 2008/0281311 A1 | 11/2008 | Dunning et al. |
| 2008/0281322 A1 | 11/2008 | Sherman et al. |
| 2008/0287943 A1 | 11/2008 | Weber et al. |
| 2009/0149850 A1 | 6/2009 | Turovskiy et al. |
| 2009/0248003 A1 | 10/2009 | Orszulak |
| 2010/0030210 A1 | 2/2010 | Paulus |
| 2010/0298822 A1 | 11/2010 | Behnke |
| 2011/0060329 A1 | 3/2011 | Gilbert et al. |
| 2011/0208179 A1 | 8/2011 | Prakash et al. |

FOREIGN PATENT DOCUMENTS

| | | |
|---|---|---|
| DE | 179607 | 3/1905 |
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4206433 | 9/1993 |
| DE | 4303882 | 8/1994 |
| DE | 4339049 | 5/1995 |
| DE | 19506363 | 8/1996 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 10 2008058737 | 4/2010 |
| DE | 102009015699 | 5/2010 |
| EP | 0 246 350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 0 521 264 | 1/1993 |
| EP | 0 556 705 | 8/1993 |

(56) References Cited

FOREIGN PATENT DOCUMENTS

| | | |
|---|---|---|
| EP | 0 558 429 | 9/1993 |
| EP | 608609 | 8/1994 |
| EP | 0659388 A1 | 6/1995 |
| EP | 0 836 868 | 4/1998 |
| EP | 0 882 955 | 12/1998 |
| EP | 1051948 | 11/2000 |
| EP | 1 159 926 | 5/2001 |
| EP | 1169976 A1 | 1/2002 |
| EP | 1 293 171 | 3/2003 |
| EP | 0 648 515 | 4/2003 |
| EP | 1366724 | 1/2006 |
| EP | 880220 | 6/2006 |
| EP | 1776929 | 4/2007 |
| EP | 1 808 144 | 7/2007 |
| EP | 2 253 286 | 11/2010 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2364461 | 7/1978 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| GB | 2214430 | 9/1989 |
| JP | 63 005876 | 1/1988 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2002-065690 | 3/2002 |
| JP | 2008142467 | 6/2008 |
| SU | 166452 | 11/1964 |
| SU | 401367 | 11/1974 |
| SU | 727201 | 4/1980 |
| WO | WO94/10922 | 5/1994 |
| WO | WO95/25472 | 9/1995 |
| WO | WO96/04860 | 2/1996 |
| WO | WO96/39086 | 12/1996 |
| WO | WO97/06739 | 2/1997 |
| WO | WO97/06740 | 2/1997 |
| WO | WO97/06855 | 2/1997 |
| WO | WO97/43971 | 11/1997 |
| WO | WO99/12607 | 3/1999 |
| WO | 99/42044 A1 | 8/1999 |
| WO | WO99/53853 | 10/1999 |
| WO | WO00/36985 | 6/2000 |
| WO | WO00/48672 | 8/2000 |
| WO | WO01/74252 | 10/2001 |
| WO | WO02/00129 | 1/2002 |
| WO | WO02/11634 | 2/2002 |
| WO | WO02/45589 | 6/2002 |
| WO | WO03/090635 | 11/2003 |
| WO | WO2004/028385 | 4/2004 |
| WO | WO2004/052182 | 6/2004 |
| WO | WO2004/083797 | 9/2004 |
| WO | WO2004/084748 | 10/2004 |
| WO | WO2005/110263 | 11/2005 |
| WO | WO2005/115235 | 12/2005 |
| WO | WO06/050888 | 5/2006 |
| WO | WO2008/012827 | 1/2008 |
| WO | WO2008/043999 | 4/2008 |
| WO | WO2008/044013 | 4/2008 |
| WO | WO08/053532 | 5/2008 |
| WO | WO2008/071914 | 6/2008 |
| WO | WO2008/110756 | 9/2008 |
| WO | 2009/065042 A2 | 5/2009 |
| WO | WO2009/075879 | 6/2009 |
| WO | WO2010/035831 | 4/2010 |

OTHER PUBLICATIONS

U.S. Appl. No. 08/483,742, filed Jun. 7, 1995, Roger A. Stern.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/400,223, filed Feb. 20, 2012, Anthony B. Ross.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,307, filed May 22, 2012, Casey M. Ladtkow.
U.S. Appl. No. 13/477,320, filed May 22, 2012, Joseph D. Brannan.
U.S. Appl. No. 13/483,858, filed May 30, 2012, Francesca Rossetto.
U.S. Appl. No. 13/488,964, filed Jun. 5, 2012, Steven P. Buysse.
U.S. Appl. No. 13/525,853, filed Jun. 18, 2012, Joseph A. Paulus.
U.S. Appl. No. 13/526,676, filed Jun. 19, 2012, Francesca Rossetto.
U.S. Appl. No. 13/539,650, filed Jul. 2, 2012, Joseph A. Paulus.
U.S. Appl. No. 13/539,690, filed Jul. 2, 2012, Steven P. Buysse.
U.S. Appl. No. 13/539,725, filed Jul. 2, 2012, Steven P. Buysse.
U.S. Appl. No. 13/539,875, filed Jul. 2, 2012, Mani N. Prakash.
U.S. Appl. No. 13/551,005, filed Jul. 17, 2012, Chris Rusin.
U.S. Appl. No. 13/567,624, filed Aug. 6, 2012, Mani N. Prakash.
U.S. Appl. No. 13/568,679, filed Aug. 7, 2012, Robert J. Behnke, II.
U.S. Appl. No. 13/596,785, filed Aug. 28, 2012, Richard A. Willyard.
U.S. Appl. No. 13/598,141, filed Aug. 29, 2012, Kenlyn S. Bonn.
U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,092, filed Jul. 19, 2011, George J. Collins.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.

(56) References Cited

OTHER PUBLICATIONS

U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.
U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/483,815, filed May 30, 2012, Jeffrey R. Unger.
U.S. Appl. No. 13/485,083, filed May 31, 2012, Robert J. Behnke, II.
U.S. Appl. No. 13/526,205, filed Jun. 18, 2012, Jeffrey L. Jensen.
U.S. Appl. No. 13/540,347, filed Jul. 2, 2012, Ronald J. Podhajsky.
U.S. Appl. No. 13/593,550, filed Aug. 24, 2012, Ronald J. Podhajsky.
U.S. Appl. No. 13/584,192, filed Aug. 13, 2012, Joseph D. Brannan.
U.S. Appl. No. 13/587,400, filed Aug. 16, 2012, James H. Orszulak.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part 1", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report"—Innovations That Work, Feb. 2002.
Humphries Jr. et al., "Finite-Element Codes to Model Electrical Heating and Non-LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).

(56) References Cited

OTHER PUBLICATIONS

Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thetmoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.

(56) References Cited

OTHER PUBLICATIONS

Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.

(56) References Cited

OTHER PUBLICATIONS

European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Oct. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009392.1 extended dated Sep. 19, 2011.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11000669.9 extended dated Jun. 30, 2011.
European Search Report EP 11001596.3 extended dated Jul. 4, 2011.
European Search Report EP 11001872.8 extended dated Jul. 6, 2011.
European Search Report EP 11004942 dated Oct. 4, 2011.
European Search Report EP 11009036.2 dated Feb. 13, 2012.
European Search Report EP 11010024.5 dated Apr. 20, 2012.
European Search Report EP 11010046.8 dated Apr. 17, 2012.
European Search Report EP 11010093.0 dated Mar. 27, 2012.
European Search Report EP 11010175.5 dated May 10, 2012.
European Search Report EP 11010176.3 dated Apr. 2, 2012.
European Search Report EP 11010177.1 dated May 10, 2012.
European Search Report EP 11174318.3 dated Nov. 7, 2011.
European Search Report EP 11185926.0 dated Feb. 3, 2012.
European Search Report EP 12000334.8 dated May 4, 2012.
European Search Report EP 12000335.5 dated May 10, 2012.
European Search Report EP 12000336.3 dated May 14, 2012.
European Search Report EP 12001841.1 dated Jul. 16, 2012.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/USO4/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Astrahan, "A Localized Current Field Hyperthermia System for Use with 192-Iridium Interstitial Implants" Medical Physics, 9 (3), May/Jun. 1982.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
International Search Report EP 04011375 dated Sep. 10, 2004.
International Search Report EP04707738 dated Jul. 4, 2007.
International Search Report—extended EP 06000708.5 dated Aug. 22, 2006.
International Search Report EP 07001484.0 dated Jun. 14, 2010.
International Search Report EP 07001494.9 dated Aug. 25, 2010.
International Search Report EP 07001494.9 extended dated Mar. 7, 2011.
International Search Report EP 07004355.9 dated May 21, 2007.
International Search Report EP08004667.5 dated Jun. 3, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09158915 dated Jul. 14, 2009.
International Search Report EP09164754.5 dated Aug. 21, 2009.

(56) References Cited

OTHER PUBLICATIONS

International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.
International Search Report EP11188798.0 dated Dec. 27, 2011.
International Search Report PCT/US03/33711 dated Jul. 16, 2004.
International Search Report PCT/US03/33832 dated Jun. 17, 2004.
International Search Report PCT/US04/02961 dated Aug. 2, 2005.
International Search Report PCT/US04/13443 dated Dec. 10, 2004.
International Search Report PCT/US09/46870 dated Jul. 21, 2009.
European Search Report for EP 13 74 0729 dated Aug. 5, 2015.
Chinese Office Action for Application No. 201380006646.4 dated Mar. 1, 2016.
Australian Examination Report for application No. 2013212609 dated Oct. 7, 2016.
Australian Examination Report No. 2 for application No. 2013212609 dated Jan. 13, 2017.

ELECTROSURGICAL DEVICE HAVING A MULTIPLEXER

BACKGROUND

1. Technical Field

The present disclosure relates to the use of energy-based ablation instruments. More particularly, the present disclosure is directed to ablation device circuitry.

2. Background of the Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such ablation procedures, e.g., such as those performed for menorrhagia, are typically done to ablate and coagulate the targeted tissue to denature or kill the tissue. Many procedures and types of devices utilizing electromagnetic radiation therapy are known in the art. Such therapy is typically used in the treatment of tissue and organs such as the prostate, heart, liver, lung, kidney, and breast.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Presently, there are several types of microwave probes in use, e.g., monopole, dipole, and helical. One type is a monopole antenna probe, which consists of a single, elongated microwave conductor exposed at the end of the probe. A probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

The typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 500 mHz to about 10 gHz is applied to a targeted tissue site to create an ablation volume, which may have a particular size and shape. Ablation volume is correlated to antenna design, antenna performance, antenna impedance, and tissue impedance. The particular type of tissue ablation procedure may dictate a particular ablation volume in order to achieve a desired surgical outcome. By way of example, and without limitation, a spinal ablation procedure may call for a longer, narrower ablation volume, whereas in a prostate ablation procedure, a more spherical ablation volume may be required.

Systems and devices used for performing ablation procedures utilize sensors to determine if the system is working properly and to control the output of the microwave ablation device. Each sensor has a power line, ground line, and a data line that returns to the source of energy or generator. However, as ablation devices evolve the number of sensors will also increase. Thus, the number of power lines, ground lines, and data lines would also increase. Existing generators may only have a single power line, ground line and data line. As such, newer ablation systems and devices may not be configured for use with existing generators.

SUMMARY

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

Electromagnetic energy is generally classified by increasing energy or decreasing wavelength into radio waves, microwaves, infrared, visible light, ultraviolet, X-rays and gamma-rays. As it is used in this description, "microwave"

generally refers to electromagnetic waves in the frequency range of 300 megahertz (MHz) ($3\times10^8$ cycles/second) to 300 gigahertz (GHz) ($3\times10^{11}$ cycles/second).

As it is used in this description, "ablation procedure" generally refers to any ablation procedure, such as, for example, microwave ablation, radiofrequency (RF) ablation, or microwave or RF ablation-assisted resection. As it is used in this description, "energy applicator" generally refers to any device that can be used to transfer energy from a power generating source, such as a microwave or RF electrosurgical generator, to tissue. For the purposes herein, the term "electrosurgical device" is interchangeable with the term "energy applicator". As it is used in this description, "transmission line" generally refers to any transmission medium that can be used for the propagation of signals from one point to another. As used in this description, transmission line may be a power line, ground line, data line, signal line, or any other line configured to transmit data or energy.

As it is used in this description, "pressure sensor" generally refers to any pressure-sensing device capable of generating a signal representative of a pressure value. For the purposes herein, the term "pressure transducer" is interchangeable with the term "pressure sensor".

Any of the herein described methods, programs, algorithms, or codes may be converted to a programming language or computer program. A "Programming Language" and "Computer Program" is any-language used to specify instructions to a computer, and includes (but is not limited to) these languages and their derivatives: Machine language, Assembler, Basic, Batch files, BCPL, C, C+, C++, Delphi, Fortran, Java, JavaScript, Machine code, operating system command languages, Pascal, Pearl, PU1, scripting languages, Visual Basic, metalanguages which themselves specify programs, and all first, second, third, fourth, and fifth generation computer languages. Also included are database and other data schemas, and any other meta-languages. For the purposes of this definition, no distinction is made between languages which are interpreted, compiled, or use both compiled and interpreted approaches. For the purposes of this definition, no distinction is made between compiled and source versions of a program. Thus reference to a program, where the programming language could exist in more than one state (such as source, compiled, object, or linked) is a reference to any and all states. The definition also encompasses the actual instructions and the intent of those instructions.

Any of the herein described methods, programs, algorithms, or codes may be contained on one or more machine-readable media. The term machine-readable medium may include a mechanism that provides (i.e., stores and/or transmits) information in a form readable by a machine such a processor, computer, or a digital processing device. For example, a machine-readable medium may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

According to at least one aspect of the disclosure herein, an electrosurgical system includes an electrosurgical generator configured to provide electrosurgical energy to an electrosurgical device coupled thereto which, in turn, delivers electrosurgical energy to tissue. The electrosurgical device includes a plurality of sensors configured to detect at least one tissue property and output a detected tissue property signal relating thereto. One or more multiplexers having a plurality of channels are electrically connected to each of the corresponding plurality of sensors. The multiplexer(s) may be configured to receive the detected tissue property signal from each sensor of the plurality of sensors and output at least one output signal along one or more signal lines. The one or more signal lines are configured to connect to the electrosurgical generator to control a power output of the electrosurgical generator. A channel select algorithm is configured to automatically select channels from the plurality of channels.

According to at least one aspect of the disclosure herein the tissue property may be selected from the group consisting of impedance, temperature, electromagnetic field, fluid pressure, fluid flow, tissue density, piezoelectric voltage, and any combination thereof.

According to another aspect of the disclosure herein, one or more of the plurality of sensors may include a sensor that outputs an analog signal. The electrosurgical system may further include an analog-to-digital converter that accepts an analog signal from one or more of the plurality of sensors and outputs a digital signal to the multiplexer.

According to another aspect of the disclosure herein, the electrosurgical system may further include an analog-to-digital converter that accepts a signal from the multiplexer(s), and outputs a digital signal to the electrosurgical generator. The channel select algorithm may include a clock and a counter configured to iterate through the channels as a function of time. The channel select algorithm may also include one or more microprocessors programmed to select a desired channel.

The channel select algorithm may be configured to transmit a binary signal to the multiplexer(s). The multiplexer(s) may be configured to select a desired channel corresponding to the binary signal.

According to yet another aspect of the disclosure herein, an energy delivery device is configured to direct energy to tissue and includes a plurality of sensors each configured to detect one or more tissue properties and output a detected tissue property signal relating thereto. One or more multiplexers having a plurality of channels are electrically connected to each of the corresponding plurality of sensors, the multiplexer(s) being configured to receive each signal relating to the respective tissue property from each sensor and output one or more output signals along a single signal line A channel select algorithm may be configured to automatically select one or more of the channels from the plurality of channels.

According to still another aspect of the disclosure herein, a method of controlling the power output of an electrosurgical system is disclosed and includes the step of sensing at least one tissue property using a plurality of sensors disposed on an electrosurgical device to create a plurality detected tissue property signals. The method further includes the steps of receiving the plurality of signals with one or more multiplexers having a plurality of channels electrically connected to each of the corresponding plurality of sensors, the one or more multiplexers configured to receive the plurality of detected tissue property signals from each of the plurality of sensors and output one or more output signals along at least one signal line; outputting a channel select signal to the multiplexer(s); selecting one of the plurality of channels based on the channel select signal; and outputting the selected signal from the multiplexer(s) along the signal line(s).

The method may further include the step of receiving the detected tissue property signal at a generator control system, the generator control system configured to modify the power output of one or more generators removably connected to the electrosurgical device as a function of the detected tissue property signal.

The method may include the step of processing the plurality of detected tissue property signals before receiving the plurality of signals at the multiplexer(s).

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
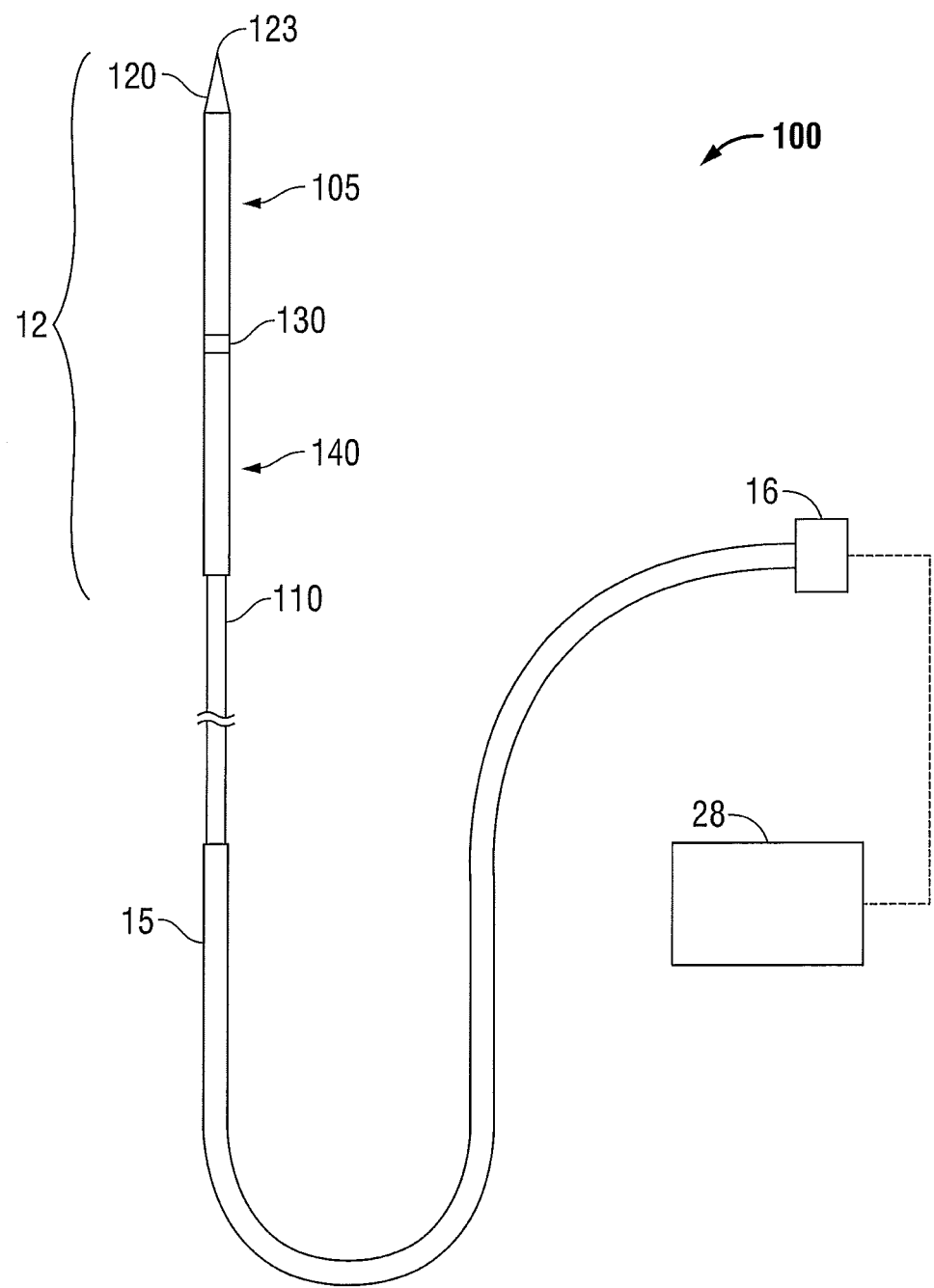
FIG. 1 shows a representative diagram of a microwave antenna assembly in accordance with at least one embodiment of the present disclosure.

Hereinafter, aspects of the presently-disclosed systems for multiplexing signals from sensor packages and methods for using the same are described with reference to the accompanying drawings. Like reference numerals may refer to similar or identical elements throughout the description of the figures.

The disclosure herein is directed to electrosurgical devices and systems for performing ablation procedures. An example of an electrosurgical system for performing an ablation procedure is depicted in FIG. 1 that shows a microwave antenna assembly 100 in accordance with one embodiment of the present disclosure. Although FIG. 1 depicts a microwave antenna assembly, the present disclosure is not limited to such an assembly. Any electrosurgical device capable of performing an ablation procedure may be used in conjunction with the embodiments described herein. Antenna assembly 100 may include a radiating portion 12 that is connected by feedline 110 (or shaft) via cable 15 to connector 16, which may further connect the assembly 10 to a power generating source 28, e.g., a microwave or RF electrosurgical generator. Assembly 100, as shown, is a dipole microwave antenna assembly, but other antenna assemblies, e.g., monopole or leaky wave antenna assemblies, may also utilize the principles set forth herein. Distal radiating portion 105 of radiating portion 12 may include a tapered end 120 which terminates at a tip 123 to allow for insertion into tissue with minimal resistance. It is to be understood, however, that tapered end 120 may include other shapes, such as without limitation, a tip 123 that is rounded, flat, square, hexagonal, cylindroconical or any other polygonal shape. An insulating puck 130 may be disposed between distal radiating portion 105 and proximal radiating portion 140. Puck 130 may be formed from any suitable elastomeric or ceramic dielectric material by any suitable process.

Power generating source 28 includes suitable input controls (e.g., buttons, activators, switches, touch screen, etc.) for controlling the power generating source 28. In addition, the power generating source 28 may include one or more display screens for providing the user with variety of output information (e.g., intensity settings, treatment complete indicators, etc.). The controls allow the user to adjust power of the energy, waveform, as well as the level of maximum energy allowed which varies depending on desired tissue effects and other parameters to achieve the desired waveform suitable for a particular task. Antenna assembly 100 may also include a plurality of input controls that may be redundant with certain input controls of the power generating source 28. Placing the input controls at the antenna assembly 100 allows for easier and faster modification of energy parameters during the ablation procedure without requiring interaction with the power generating source 28.

As will be described in more detail below, FIGS. 2-6 depict different electrosurgical devices capable of consolidating all sensor-to-generator communication onto a limited number of signal lines. The power supply and ground lines for the sensor packages will be provided by a single power supply line and common ground line to the device from the generator. The electrosurgical devices described herein apply to generators which can read in a limited number of analog or digital sensor lines. As an example, a microwave ablation (MWA) system may have a thermocouple sensor on the device side, which is a passive analog device. The generator is able to see the thermocouple voltage through a twisted wire pair which it amplifies and monitors (one of the wires being a ground or reference line). For a device which has multiple sensor packages, all the sensor data must pass to the generator through this signal analog signal line.

To consolidate all sensor output signals onto a limited amount of lines, a multiplexer is used within the electrosurgical device handle. All sensors output analog or digital signals that are input into the multiplexer. The multiplexer cycles through the input signals from the sensor packages, according to a channel select algorithm, and outputs the corresponding signal onto the signal line which goes to the generator.

Figure 2:
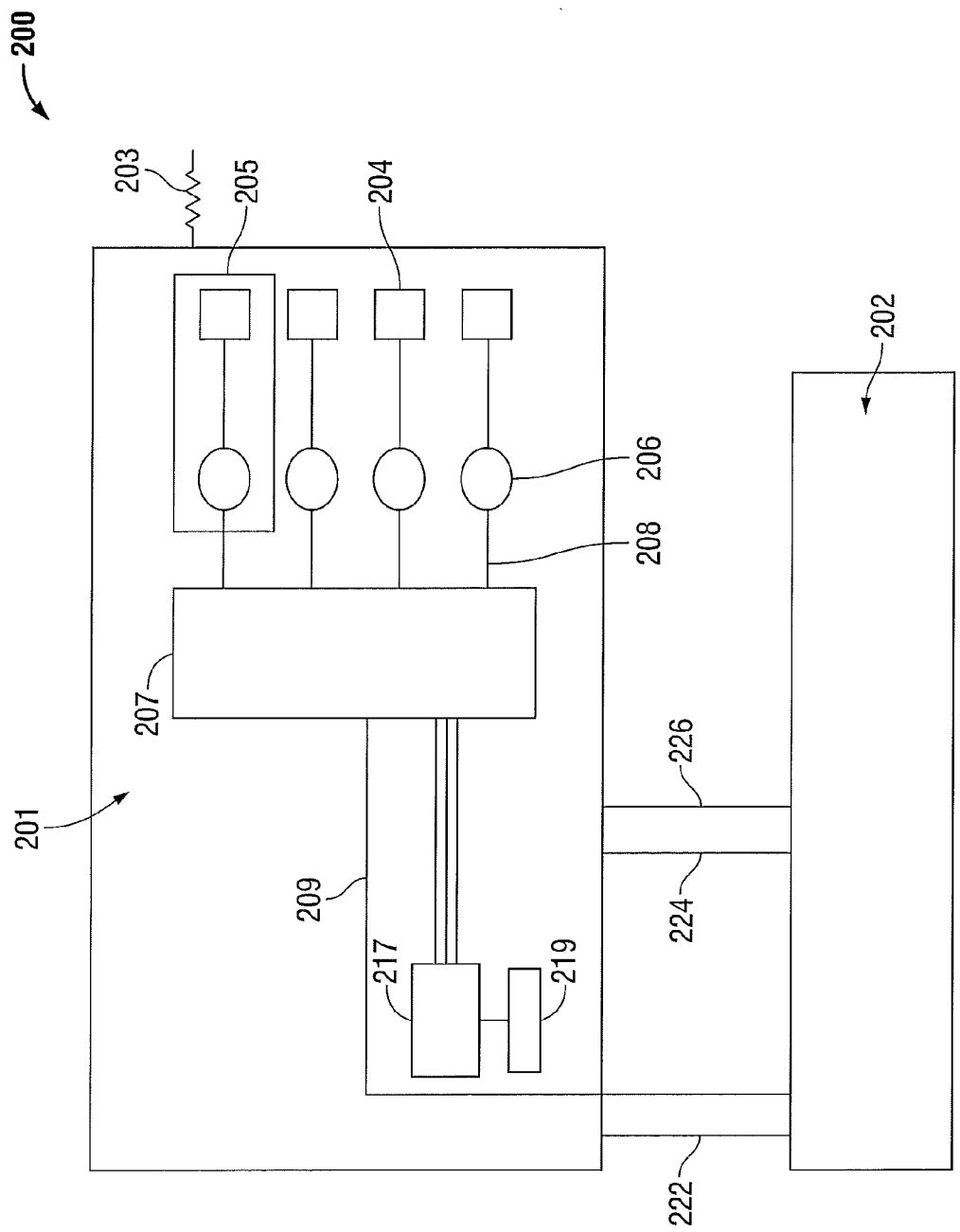
FIG. 2 is a block diagram view of an ablation system according to an embodiment of the present disclosure.

Referring to FIG. 2, an electrosurgical system 200 includes an electrosurgical device 201 and generator 202. Electrosurgical device 201 includes an ablation antenna 203 for outputting radiation to ablate tissue, e.g., mammalian tissue. Antenna 203 is coupled to generator 202 via a high power transmission line 222. In other embodiments, generator 202 may be integrated into electrosurgical device 201. Generator 202 may have at least one control system for monitoring and controlling power output to antenna 203. Antenna 203 may be optimized for any desired frequency band. Antenna 203 may be removably coupled to electrosurgical device 201 and/or generator 202.

Electrosurgical device 201 includes a plurality of sensors 204 for detecting one or more tissue properties. Non-limiting examples of at least one of the plurality of sensors 204 may include thermal sensors, electromagnetic field sensors, RF electrode impedance monitors, user interface electronics, fluid pressure sensors, fluid flow sensors, piezoelectric voltage sensors, ultrasound and/or optical sensors for detecting tissue density, and any combinations thereof. The sensors 204 may output an analog electrical signal, a digital signal, or a combination thereof. Each sensor 204 outputs a signal indicative of a detected tissue property or detected property of the ambient environment as an analog electrical signal or a digital signal. The detected properties include, but are not limited to: impedance, temperature, electromagnetic field, tissue density etc.

One or more of the plurality of sensors may be included in one or more sensor packages 205. In one embodiment, sensor package 205 may include one or more signal processing circuits 206 for conditioning the signal that is output from the sensor. A signal processing circuit 206 may include various integrated circuits and/or discrete components to process the output of sensor 204 such as low noise amplifiers, voltage dividers, etc. In another embodiment, signal processing circuit 206 may be configured to modify the output of each sensor 204 in one or more ways that include, but are not limited to, any type of analog or digital modification or conversion such as amplification and/or analog-to-digital conversion. For example, for sensors that output analog signals, the output of each sensor 204 may be conditioned using an analog signal processing circuit by amplification or analog-to-digital conversion.

The signal outputted by each sensor 204 may be used to determine if the sensors are functioning properly by measuring the voltage of the signal and comparing the measured voltage to a predetermined voltage. This could be modeled as a step function wherein if the proper voltage is met, the system knows the sensor is working and vice versa. For example, the output of each sensor 204 may be conditioned using an analog signal processing circuit as described above to output 3 volts +/− an acceptable error. If the voltage is read to be outside of this range, then generator 202 may realize there is an error and respond accordingly. In an error situation, a signal may be given to an alert system, such as a light or audio device (not shown) that would notify the user of a faulty sensor or generator may cease delivery of energy to the electrosurgical device 201.

Multiplexer 207 is electrically coupled to each sensor package 205 and/or analog signal processing circuit 206 and is configured to receive the signals from each sensor package 205. Multiplexer 207 has multiple channels with at least one channel corresponding to each sensor package 205. Multiplexer 207 may be an analog multiplexer, a digital multiplexer, or a combination thereof. Multiplexer 207 outputs a signal along at least one signal line 209. The output signal may be any one or more of the signals generated by the sensor packages 205 and/or analog signal processing circuits 206. Thus, the multiplexer 207 may accept multiple signals, select a channel corresponding to a sensor package 205 or sensor 204, and output an output signal along the limited number of signal lines 209, thus reducing the amount of lines that ultimately connect electrosurgical device 201 to generator 202. As an example, an electrosurgical device 201 may have N sensors 204 and up to N−1 signal lines 209, thus requiring one or more multiplexers 207 as described above to utilize the reduced amount of signal lines 209 relative to the amount of sensors 209.

Signal line 209 is configured to ultimately connect to generator 202 to provide feedback. Based on the feedback provided by signal line 209, generator 202 controls the energy output of generator 202 to antenna 203. In embodiments, such as that shown in FIG. 2, signal line 209 may connect directly to generator 202 without having to pass through any other stages or may pass through one or more circuits to process the signal. Generator 202 also provides a power line 224 and a reference/ground line 226 to provide power to multiplexer 207, analog signal processing circuits 206, and sensor packages 205.

Electrosurgical device 201 may also include a channel select system that includes channel select lines 215, a counter 217, and a clock 219. Clock 219 may be a crystal oscillator that outputs a signal at a predetermined frequency. The signal provided by clock 219 is used to increment counter 217 that outputs the required binary representation to select one of the input channels 208 to output a detected tissue property associated with the selected input channel For example, as shown in FIG. 2, counter 217 would output a 3-bit binary signal in the case of an 8 to 1 multiplexer. Clock 219 and counter 217 may be used to cycle through input channels 208 as a function of time.

The channel select system may include a channel select algorithm for automatically selecting one or more channels. The algorithm may have a selection function such that the multiplexer selects channels as a function of a selected variable including but not limited to time, relative location of the electrosurgical device, any desired tissue property as described herein, temperature, impedance, EM field, or any combination thereof. The algorithm includes computing the selection function, selecting the channel(s), and outputting a signal from the selected channel(s) along the signal line(s).

Figure 3:
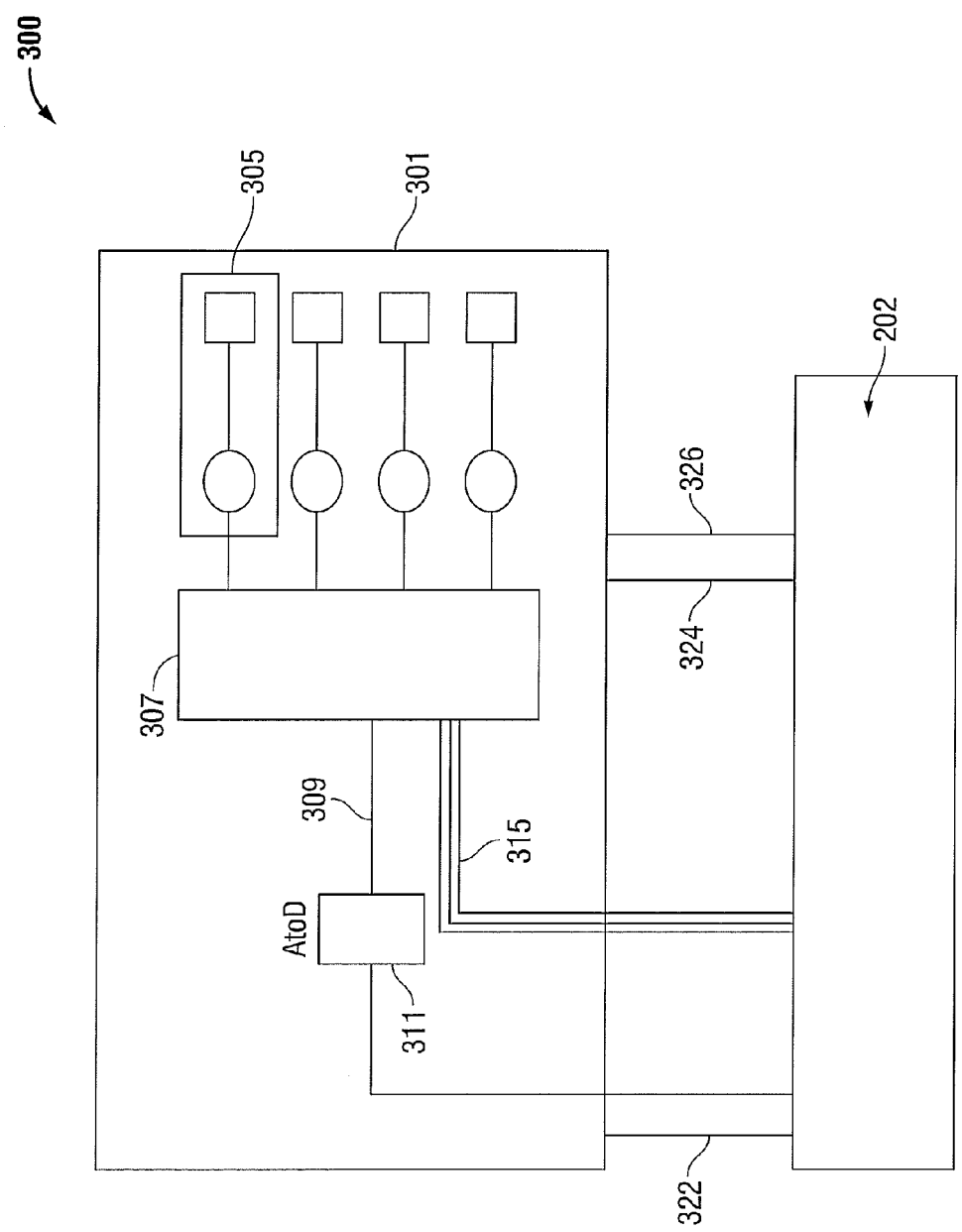
FIG. 3 is a block diagram view of an ablation system according to another embodiment of the present disclosure.

Turning to FIG. 3, an electrosurgical system 300 according to another embodiment of the present disclosure is shown generally as 301. In the interest of brevity, the present embodiment will focus on the differences between the previously described electrosurgical system 200 and electrosurgical system 300. Electrosurgical system 300 includes an electrosurgical device 301 electrically coupled to generator 302. During an electrosurgical procedure, i.e. an ablation procedure, a clinician may want to monitor a particular tissue property. By operating the controls on generator 302, the clinician may select the desired tissue property. Then generator 302 may provide a binary signal along channel select lines 315 directly to microprocessor 207 to select an input channel 208 corresponding to the sensor package 205 that detects the desired tissue property.

Multiplexer 207 then selects the input channel 208 corresponding to the desired tissue property using a channel select system and/or channel select algorithm and outputs an analog detected tissue property signal indicative of the desired tissue property on signal line 309. Signal line 309 may provide the analog signal directly to generator 302 or the analog signal may be converted to a digital signal using an analog to digital (A/D) converter 311 before electrosurgical device 301 outputs the signal to generator 302.

Figure 4:
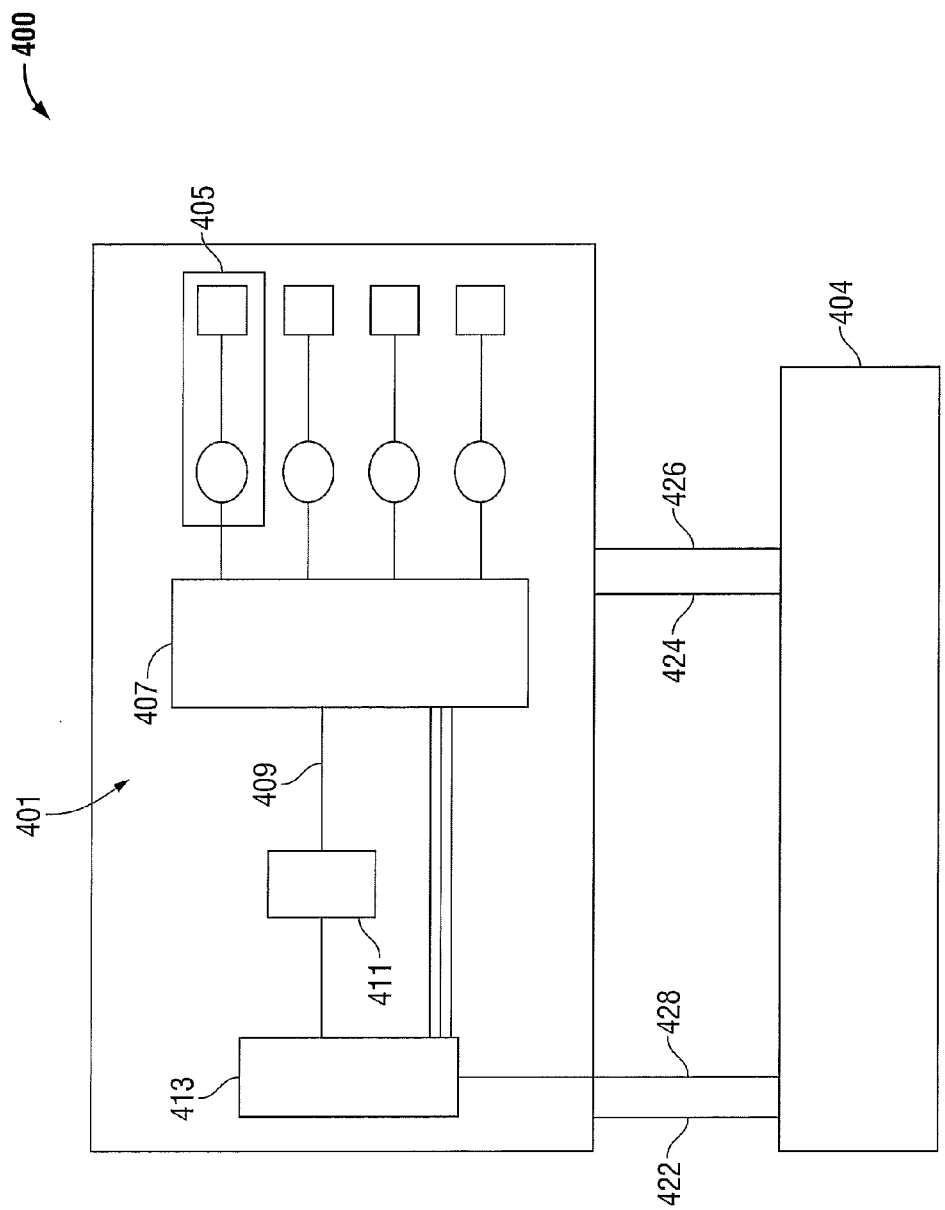
FIG. 4 is a block diagram view of an ablation system according to yet another embodiment of the present disclosure.

Turning to FIG. 4, an electrosurgical system according to another embodiment of the present disclosure is shown generally as 400. In the interest of brevity, the present embodiment will focus on the differences between the previously described electrosurgical systems 200, 300 and electrosurgical system 400. Electrosurgical system 400 includes an electrosurgical device 401 coupled to generator 402. Generator 402 provides a reference or ground 422, a power line 424, and a communication line 426. Communication line 426, which will be described in more detail below, is configured to provide a two way digital data stream between generator 402 and microprocessor 413 of electrosurgical device 401.

Signal line 409 may pass directly or indirectly to one or more microprocessors 413. In some embodiments where the output signal from multiplexer 407 is analog, the signal line 409 may connect to an analog-to-digital converter 411 that converts the analog signal to a digital signal before outputting the signal to microprocessor 413. If the output signal from multiplexer 407 is already digital, then the output signal may pass directly to the microprocessor 413.

Figure 5:
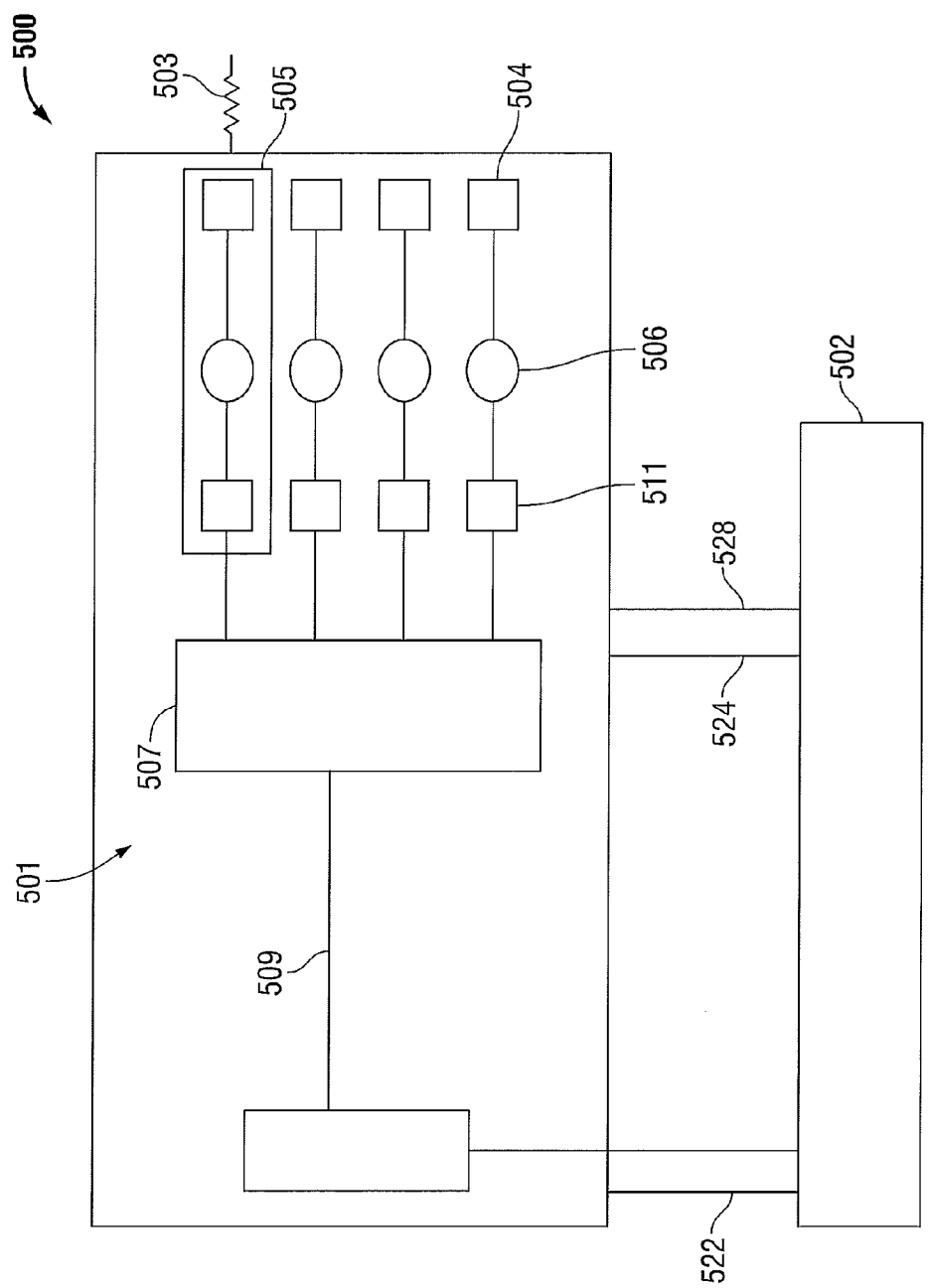
FIG. 5 is a block diagram view of an ablation system according to yet another embodiment of the present disclosure.

Turning to FIG. 5, an electrosurgical system according to another embodiment of the present disclosure is shown generally as 500 In the interest of brevity, the present embodiment will focus on the differences between the previously described electrosurgical systems 200, 300, 400 and electrosurgical system 500. Electrosurgical system 500 includes an electrosurgical device 501 coupled to generator 502. Generator 402 provides a reference or ground 522, a power line 524, and a communication line 526. Communication line 526, which will be described in more detail below, is configured to provide a two way digital data stream between generator 502 and microprocessor 513 of electrosurgical device 501. In some embodiments, sensor package 505 includes at least one sensor 504 as described above, at least one signal processing circuit 506 as described above, and at least one analog to digital converter 511 as described above. As shown, electrosurgical device includes a multiplexer 507 configured to accept either analog or digital signals from the sensor packages 505 and to output a digital signal along signal line 509 to the microprocessor 513. Microprocessor 513 and multiplexer 507 may be configured to digitally control channel selection of multiplexer 507 channels over the signal line 509, thus reducing the amount of internal hard wiring.

Figure 6:
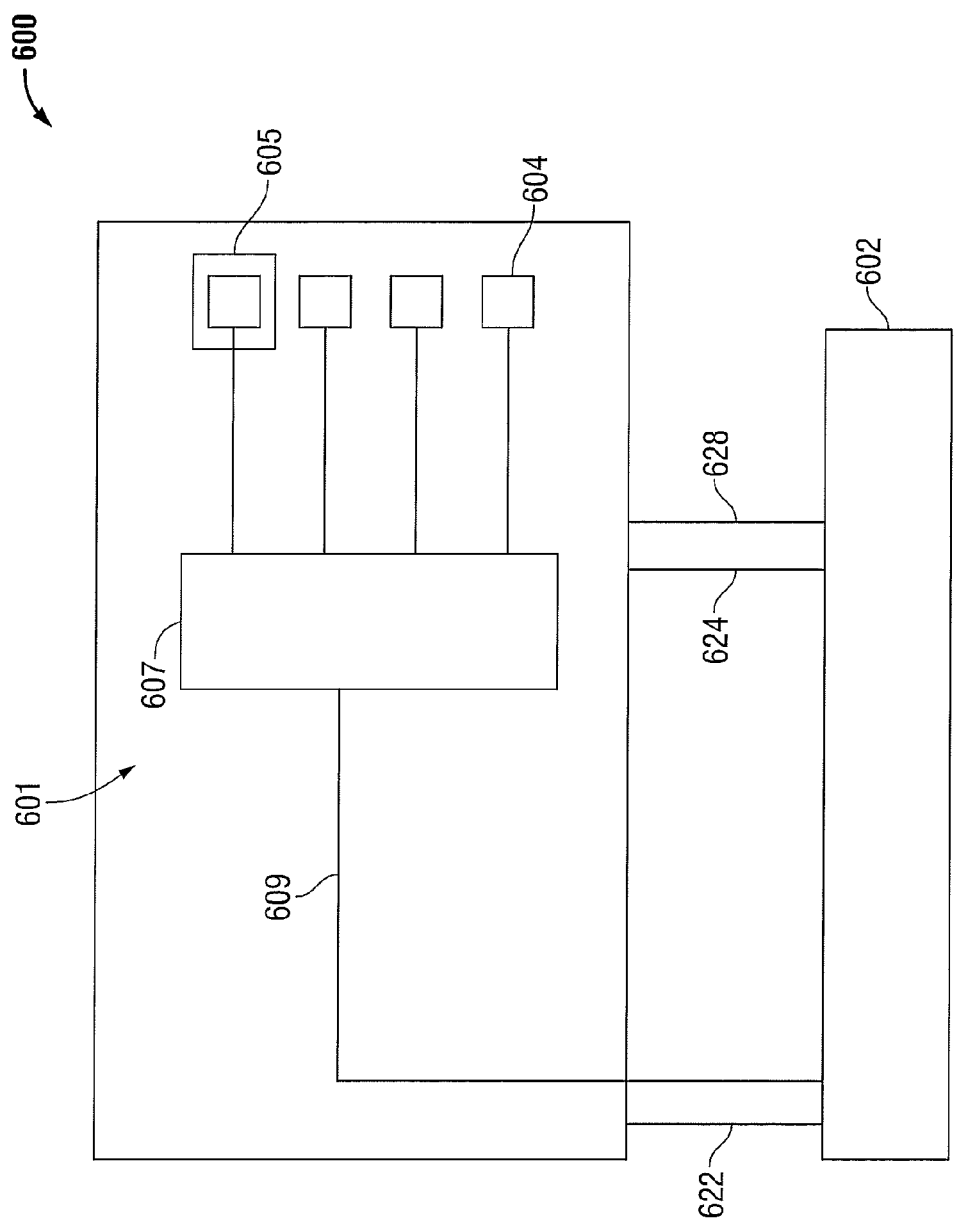
FIG. 6 is a block diagram view of an ablation system according to yet another embodiment of the present disclosure.

Turning to FIG. 6, an electrosurgical system according to another embodiment of the present disclosure is shown generally as 600 In the interest of brevity, the present embodiment will focus on the differences between the previously described electrosurgical systems 200, 300, 400, 500 and electrosurgical system 600. Electrosurgical system 600 includes an electrosurgical device 601 coupled to generator 602. Generator 602 provides a reference or ground 622, a power line 624, and a digital signal line 609. Digital signal line 609, which will be described in more detail below, is configured to provide a two way digital data stream between generator 602 and digital multiplexer 607 of electrosurgical device 601. As shown, electrosurgical device 601 includes a multiplexer 607 configured to accept either analog or digital signals from the sensor packages 605 and to output a digital signal directly to the generator 602. In such a case, multiplexer 607 may be integrated with a microprocessor to handle all communication protocol with the generator 602 and to control channel selection of the multiplexer channels.

Electrosurgical system may one or more generators for supplying energy and one or more generator control systems for controlling a power output of the generator(s). The generator control system(s) may include one or more computer readable media and control software stored thereon. The electrosurgical system may also have an electrosurgical device as described above.

A two way digital data stream may be created over a signal line or communication line as described above. The two way digital data stream may include data from one or more sensors, from one or more multiplexers, from one or more microprocessors, or from one or more generators.

Further disclosed is a method of controlling the power output of an electrosurgical device. The method has the step of sensing one or more tissue properties using a plurality of sensors disposed on an electrosurgical device as described above to create a plurality of detected tissue property signals. At least one of the plurality of signals comes from each sensor.

The method further includes the step of receiving the plurality of analog or digital signals at a multiplexer as described above. In some embodiments, the plurality of input signals may be modified or converted to digital before being received at the multiplexer.

The method may further include the step of selecting which of the plurality of signals to allow the multiplexer to output by using a channel select system and/or channel select algorithm as described above. For example, the channel select system/algorithm may output a channel select signal to the multiplexer, allowing selection of one of the plurality of signals based on the channel select signal.

In some embodiments, the method may include outputting a selected analog signal from the multiplexer. In other embodiments, the signal output may be digital.

The method may further include the step of receiving a data signal at a generator control system. The data signal may be an analog signal or digital signal that either comes from the multiplexer directly or passes through one or more circuit components, modifications, and/or conversions. The generator control system may be configured to modify the power output of one or more generators as a function of the data signal. The generator(s) may be removably connected to the electrosurgical device such that there may be a detachable power supply line, a detachable signal line or communication line as described above, a detachable ground wire, or any combination thereof.

The method may further include the step of processing the plurality of analog signals as described above before receiving the plurality of analog signals at the multiplexer. In some embodiments, the method further includes the steps of converting an analog signal to a digital signal, and receiving a digital signal at one or more microprocessors as describe above. Again, as described above, the channel select system may be disposed within the electrosurgical device or the generator control system.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawing figs. are presented only to demonstrate certain examples of the disclosure. Other elements, steps, methods, and techniques that are insubstantially different from those described above and/or in the appended claims are also intended to be within the scope of the disclosure.

What is claimed is:

1. An electrosurgical system, comprising:
   an electrosurgical generator configured to provide electrosurgical energy to an electrosurgical device coupled thereto which, in turn, is configured to deliver electrosurgical energy to tissue, the electrosurgical device including:
   a plurality of sensors configured to detect at least one tissue property and output a detected tissue property signal relating thereto;
   at least one multiplexer having a plurality of channels, each channel of the plurality of channels electrically connected to a respective sensor of the plurality of sensors, the at least one multiplexer configured to receive the detected tissue property signal from each sensor of the plurality of sensors and output at least one output signal along at least one signal line, wherein the at least one signal line is configured to connect to the electrosurgical generator to control a power output of the electrosurgical generator;
   user-operated controls associated with the electrosurgical generator configured to select at least one variable from the group consisting of temperature, impedance, electromagnetic field, fluid pressure, tissue density, and piezoelectric voltage; and a channel select system configured to select at least one channel from the plurality of channels as a function of the at least one user-selected variable.

2. The electrosurgical system of claim 1, wherein the tissue property is selected from the group consisting of impedance, temperature, electromagnetic field, fluid pressure, tissue density, and piezoelectric voltage.

3. The electrosurgical system of claim 1, wherein the at least one of the plurality of sensors includes a sensor that outputs an analog signal.

4. The electrosurgical system of claim 3, further comprising an analog-to-digital converter that accepts an analog signal from at least one of the plurality of sensors and outputs a digital signal to the multiplexer.

5. The electrosurgical system of claim 3, further comprising an analog-to-digital converter that accepts a signal from the multiplexer, and outputs a digital signal to the electrosurgical generator.

6. The electrosurgical system of claim 1, wherein the channel select system includes at least one clock and a counter configured to iterate through the channels as a function of time.

7. The electrosurgical system of claim 1, wherein the channel select system includes at least one microprocessor programmed to select a desired channel.

8. The electrosurgical system of claim 1, wherein the channel select system transmits a binary signal to the at least one multiplexer, the at least one multiplexer configured to select a desired channel corresponding to the binary signal.

9. The electrosurgical system of claim 1, wherein the user operated controls are disposed on the electrosurgical generator.

10. The electrosurgical system of claim 1, wherein the user operated controls are disposed on the electrosurgical device.

11. An electrosurgical device configured to direct energy to tissue, comprising:
a plurality of sensors each configured to detect at least one tissue property and output a detected tissue property signal relating thereto;
at least one multiplexer having a plurality of channels, each channel of the plurality of channels electrically connected to a respective sensor of the plurality of sensors, the at least one multiplexer configured to receive each signal relating to the respective tissue property from each sensor and output at least one output signal along a single signal line;
user operated controls configured to select at least one variable from the group consisting of temperature, impedance, electromagnetic field, fluid pressure, tissue density, and piezoelectric voltage; and
a channel select system configured to select at least one channel from the plurality of channels as a function of the at least one user-selected variable.

12. A method of controlling a power output of an electrosurgical system, comprising:
sensing at least one tissue property using a plurality of sensors disposed on an electrosurgical device to create a plurality of detected tissue property signals, at least one of the plurality of detected tissue property signals from each sensor;
receiving the plurality of detected tissue property signals with at least one multiplexer having a plurality of channels, each channel of the plurality of channels electrically connected to a respective sensor of the plurality of sensors, the at least one multiplexer configured to receive the plurality of detected tissue property signals from each of the plurality of sensors and output at least one output signal along at least one signal line, the at least one multiplexer disposed within the electrosurgical device;
selecting a user-selectable variable from a group consisting of temperature, impedance, electromagnetic field, fluid pressure, tissue density, and piezoelectric voltage using user operated controls associated with the electrosurgical device;
outputting a channel select signal to the at least one multiplexer as a function of the user-selected variable;
selecting one of the plurality of channels based on the channel select signal; and
outputting a selected signal from the at least one multiplexer along the at least one signal line.

13. The method of claim 12, further comprising receiving the selected signal at a generator control system, the generator control system configured to modify a power output of at least one generator removably connected to the electrosurgical device as a function of the detected tissue property signal.

14. The method of claim 13, further comprising processing the plurality of detected tissue property signals before receiving the plurality of detected tissue property signals at the multiplexer.

15. The method of claim 13, wherein using user operated controls includes using user operated controls disposed on the electrosurgical generator system to select the user-selectable variable.

16. The method of claim 12, wherein using user operated controls includes using user operated controls disposed on the electrosurgical device to select the user-selectable variable.

* * * * *